(12) United States Patent
Konerding et al.

(10) Patent No.: US 10,354,748 B1
(45) Date of Patent: Jul. 16, 2019

(54) STORING GENETIC DATA IN A STORAGE SYSTEM

(71) Applicant: Google Inc., Mountain View, CA (US)

(72) Inventors: David Konerding, San Mateo, CA (US); Jeffrey Adgate Dean, Palo Alto, CA (US); Sanjay Ghemawat, Mountain View, CA (US); Jonathan Bingham, Milpitas, CA (US)

(73) Assignee: Google LLC, Mountain View, CA (US)

( * ) Notice: Subject to any disclaimer, the term of this patent is extended or adjusted under 35 U.S.C. 154(b) by 565 days.

(21) Appl. No.: 14/671,167

(22) Filed: Mar. 27, 2015

Related U.S. Application Data

(60) Provisional application No. 61/971,803, filed on Mar. 28, 2014.

(51) Int. Cl.
*G16B 50/00* (2019.01)
*G06F 16/13* (2019.01)
*G06F 16/28* (2019.01)
*G06F 16/174* (2019.01)

(52) U.S. Cl.
CPC ............ *G16B 50/00* (2019.02); *G06F 16/13* (2019.01); *G06F 16/1744* (2019.01); *G06F 16/285* (2019.01)

(58) Field of Classification Search
CPC ......... G06F 17/60091; G06F 17/30091; G06F 17/30153; G06F 17/30598
See application file for complete search history.

(56) References Cited

PUBLICATIONS

Deutsch, Network Working Group RFC1951, May 1996; https:tools.ietf.org/html/rfc1951, last accessed Sep. 30, 2017. (Year: 1996).*
Ramirez-Gomez et al., (Source Code for Biology and Medicine, 2012,7:6; http: www.scfbm.org/content/7/1/6; last accessed Sep. 30, 2017). (Year: 2012).*
Clarke et al, (Nature Methods. May 2012;5(5)1-4, ePub Apr. 27, 2012) (Year: 2012).*
Li et al., (Bioinformatics Applications Note. 2009;25(16):2078-2079). (Year: 2009).*
Wong et al., Transposition Algorithms on Very Large Compressed Databases, 12th International Conference on Very Large Databases, Kyoto, Japan, Aug. 25-28, 1986.*

* cited by examiner

*Primary Examiner* — Aaron A Priest
(74) *Attorney, Agent, or Firm* — Honigman LLP; Brett A. Krueger

(57) ABSTRACT

A method includes receiving, by a processing device, a plurality of genome files. Each genome file corresponds to a different sample and defining a genetic sequence. The method also includes generating, by the processing device, a two-dimensional alignment file based on the genome files and a reference sequence. A first dimension of the alignment file corresponds to individual genetic sequences and each of the genetic sequences is aligned with respect to the reference sequence along a second dimension of the alignment file. The method includes separating, by the processing device, the alignment file into a plurality of groups and storing the groups in a non-transitory genome data store. Each group contains segments of the genetic sequences of two or more of the genomic files.

14 Claims, 7 Drawing Sheets

Specification includes a Sequence Listing.

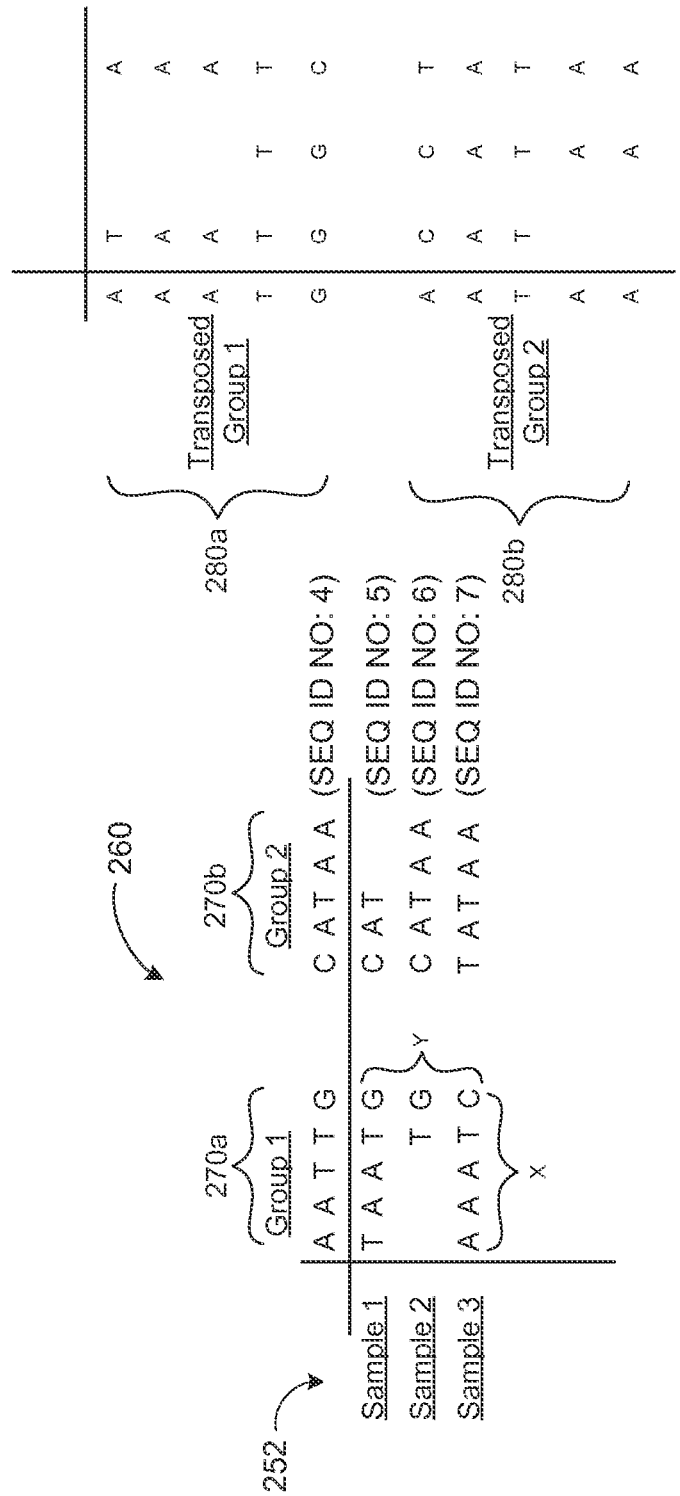

STORING GENETIC DATA IN A STORAGE SYSTEM

This U.S. patent application claims priority under 35 U.S.C. § 119(e) to U.S. Provisional Application 61/971,803, filed on Mar. 28, 2014, which is hereby incorporated by reference in its entirety.

This application incorporates by reference in its entirety the Sequence Listing entitled "Sequence_Listing_ST25.txt" (1.87 kilobytes), which was created on Jul. 27, 2015 and filed electronically herewith.

TECHNICAL FIELD

This disclosure relates to techniques for storing genetic data in a data storage system.

BACKGROUND

Deoxyribonucleic acid (DNA) sequence data volumes are increasing rapidly. In some scenarios, the inability to efficiently store and retrieve DNA sequence data can impact scientific progress.

SUMMARY

One aspect of the disclosure provides a method that includes receiving, by a processing device, a plurality of genome files. Each genome file corresponds to a different sample and defining a genetic sequence. The method also includes generating, by the processing device, a two-dimensional alignment file based on the genome files and a reference sequence. A first dimension of the alignment file corresponds to individual genetic sequences and each of the genetic sequences is aligned with respect to the reference sequence along a second dimension of the alignment file. The method includes separating, by the processing device, the alignment file into a plurality of groups and storing the groups in a non-transitory genome data store. Each group contains segments of the genetic sequences of two or more of the genomic files.

Implementations of the disclosure may include one or more of the following features. In some implementations, storing the groups includes, for each group, transposing the group into a transposed group such that the segments of each genetic sequence in the transposed group are aligned with a corresponding portion of the reference sequence along the first dimension and storing the transposed groups in the genome data store. Storing the transposed groups may include, for each transposed group, generating a group string based on the transposed group. The group string includes the contents of the transposed group. Storing the transposed groups may further include compressing the group strings into compressed files and storing the compressed files in the genome data store. The group strings may be compressed using the Flate compression algorithm.

In some implementations, storing the transposed groups includes, for each transposed group, generating a group string based on the transposed group and generating a master string based on the group strings. The group string includes the contents of the transposed group, and the master string represents the entire contents of the alignment file. Storing the transposed groups may further include compressing the master string into a compressed file and storing the compressed file in the genome data store. The master string may be compressed using the Flate algorithm. Moreover, the plurality of genome files may be binary sequence alignment/map (BAM) files.

Another aspect of the disclosure provides a data storage system that includes a storage system in communication with a processing device. The storage system has one or more non-transitory computer readable mediums and stores a genome data store. The processing device executes computer readable instructions causing the processing device to receive a plurality of genome files, each genome file corresponding to a different sample and defining a genetic sequence, and generate a two-dimensional alignment file based on the genome files and a reference sequence. A first dimension of the alignment file corresponds to individual genetic sequences and each of the genetic sequences is aligned with respect to the reference sequence along a second dimension of the alignment file. The computer readable instructions also cause the processing device to separate the alignment file into a plurality of groups and store the groups in the genome data store. Each group contains segments of the genetic sequences of two or more of the genomic files.

In some implementations, storing the groups includes, for each group, transposing the group into a transposed group such that the segments of each genetic sequence in the transposed group are aligned with a corresponding portion of the reference sequence along the first dimension and storing the transposed groups in the genome data store. Storing the transposed groups may include, for each transposed group, generating a group string based on the transposed group. The group string includes the contents of the transposed group. Storing the transposed groups may further include compressing the group strings into compressed files and storing the compressed files in the genome data store. The group strings may be compressed using the Flate compression algorithm.

In some implementations, storing the transposed groups includes, for each transposed group, generating a group string based on the transposed group and generating a master string based on the group strings. The group string includes the contents of the transposed group, and the master string represents the entire contents of the alignment file. Storing the transposed groups may further include compressing the master string into a compressed file and storing the compressed file in the genome data store. The master string may be compressed using the Flate algorithm. Moreover, the plurality of genome files may be BAM files.

Yet another aspect of the disclosure provides a method for reading genetic sequence data from a data storage system. The method includes receiving, by a processing device, a read request from a requesting computing device. The read request indicates a genetic sequence identifier that indicates a requested genetic sequence and a read offset corresponding to a segment of the requested genetic sequence. The method includes retrieving, by the processing device, one or more compressed files corresponding to the requested genetic sequence from the data storage system, decompressing the one or more compressed files to obtain one or more transposed groups, and de-transposing the one or more transposed groups into one or more de-transposed groups. The method also includes reading, by the processing device, the segment of the requested genetic sequence from the one or more de-transposed groups based on the genetic sequence identifier and the read offset and transmitting the read segment of the requested genetic sequence to the requesting computing device.

In some implementations, decompressing the one or more compressed files includes decompressing the one or more compressed files into a master string representing an entire set of genomic data and identifying one or more relevant group strings in the master string and reassembling the one or more relevant group strings into the one or more transposed groups. The relevant group strings correspond to the genetic sequence identifier and the read offset. Moreover, each relevant group string defines a unique subset of the entire collection of the genomic data. Additionally or alternatively, decompressing the one or more compressed files includes decompressing the one or more compressed files into one or more relevant group strings and reassembling the one or more relevant group strings into the one or more transposed groups. The relevant group strings group strings correspond to the genetic sequence identifier and the read offset. Moreover, each relevant group string defines a unique subset of an entire collection of genomic data.

In some examples, the read offset identifies a group of the one or more groups and reading the segment of the requested genetic sequence includes reading all of the genetic data corresponding to the requested genetic sequence from the group. The read offset may identify a starting location of a read with respect to a reference sequence and the read request may include an end location of the read with respect to the reference sequence. In such examples, reading the segment of the requested genetic sequence includes reading the genetic data corresponding to the requested genetic sequence from the one or more groups that begins at the starting location and ends at the end location. Transmitting the read segment may include generating a BAM file based on the read segment and transmitting the BAM file to the requesting computing device.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2C is a schematic view illustrating an example alignment file separated into groups.

FIG. 2D is a schematic view illustrating an example of transposed groups.

Like reference symbols in the various drawings indicate like elements.

DETAILED DESCRIPTION

Figure 1A:
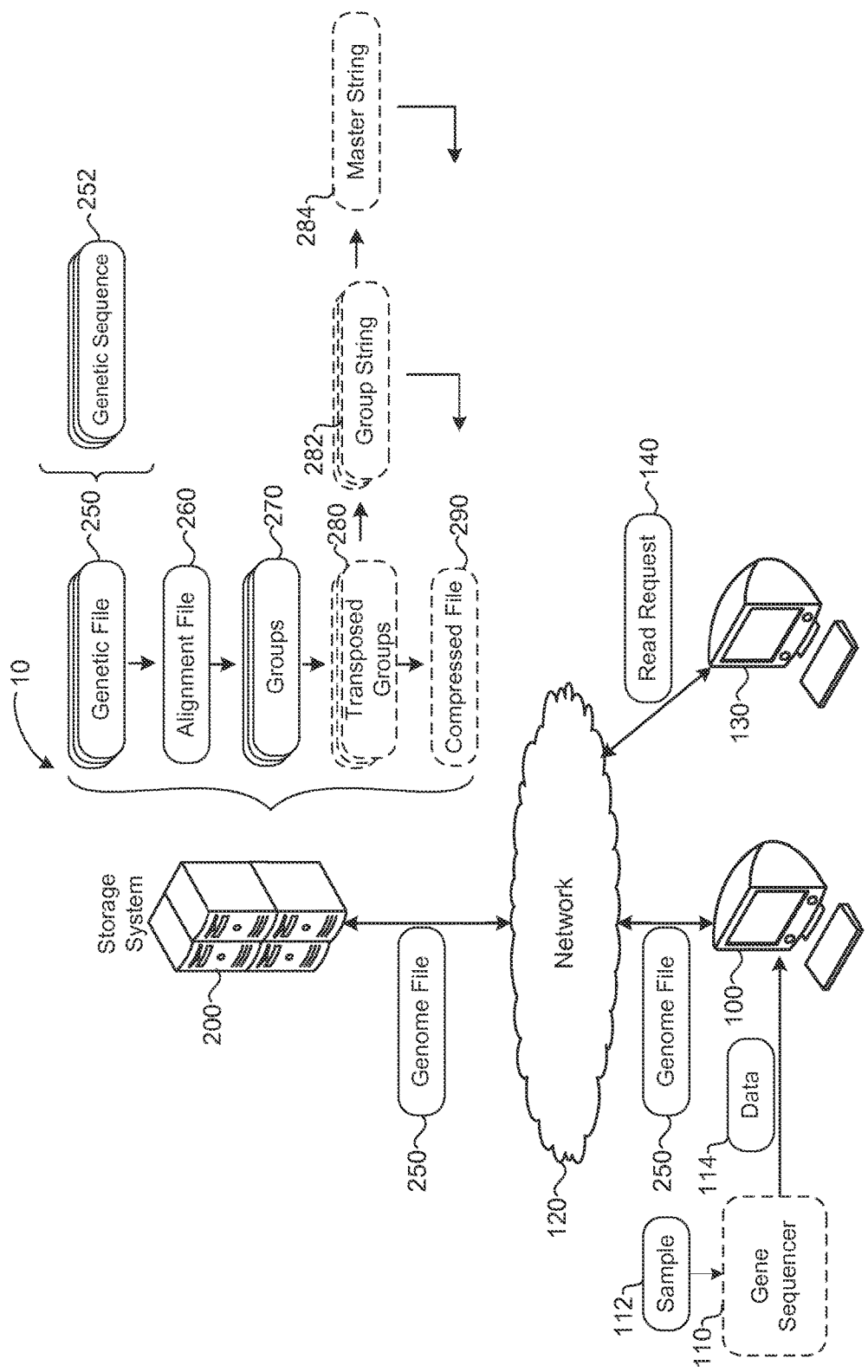
FIG. 1A is a schematic view illustrating an example system for storing genetic sequence data.

FIG. 1A illustrates an example system 10 for storing genetic sequence data 114. The system 10 includes a data storage system 200 that stores genetic data received from one or more source computing devices 100. The data storage system 200 can be further configured to respond to read requests 140 from one or more requesting computing devices 130. A requesting computing device 130 can be a source computing device 100 and vice-versa. In some implementations, the data storage system 200 communicates with source computing devices 100 and requesting computing devices 130 over a network 120 (e.g., the Internet and/or an intranet). Additionally or alternatively, the data storage system 200 can communicate directly with a requesting computing device 130 or a source computing device 100 (e.g., via a USB connection or Bluetooth(r) connection).

A source computing device 100 can receive output of a gene sequencer 110 and can generate a genome file 250 based on the output of the gene sequencer 110. The output of the gene sequence can include genetic sequence data 114 corresponding to a sample 112. The source computing device 100 can create the genome file 250 based on the genetic sequence data 114. Each genome file 250 can store genetic sequence data 114 corresponding to a single genetic sample 112 (e.g., a DNA sample). A genome file 250 can include a series of nucleobases (e.g., T, A, G, or C) aligned to a reference sequence, the series of nucleobases representing a genetic sequence indicated in the genetic sequence data 114 corresponding to the sample 112. A reference sequence is a predetermined string of nucleobases. A reference sequence is a segment (or an entire) of a representative example of a species set of genes. A reference sequence does not necessarily represent the set of genes of a single sample provider. Rather, a reference sequence can represent a haploid mosaic of different DNA sequences from a number of donors. The source computing device 100 and/or the gene sequencer 110 can add additional information to the genome file 250, such as a sample identifier. In some implementations, the genome file 250 is in a BAM file format or in any other suitable format (e.g., a SAM file). SAM stands for Sequence Alignment/Map format, and BAM is the binary version of a SAM file. A SAM file is a tab-delimited text file that contains sequence alignment data.

The source computing device 100 uploads the genome file 250 to a data storage system 200. In operation, the source computing device 100 may upload a plurality of the genome files 250 to the data storage system 200. Each genome file 250 can correspond to a different sample 112 collected in, for example, a study. Furthermore, while one source computing device 100 is shown in FIG. 1A, more than one source computing device 100 can upload genome files 250 to the data storage system 200.

The data storage system 200 includes one or more computing devices and is configured to receive genome files 250 from one or more source computing devices 100. In some implementations, the data storage system 200 is a networked and/or clustered file system.

In order to store large amounts of genetic sequence data 114 more efficiently, the data storage system 200 collects a set of related genome files 250 and generates an alignment file 260 based on the set of related genome files 250. An alignment file 260 stores the genetic sequence data 114 of each of the genome files 250 in relation to the reference sequence 262 (FIG. 2B). The set of related genome files 250 can, for example, correspond to a collection of samples 112 collected in a study or research undertaking. In some implementations, the alignment file 260 includes a two-dimensional data structure (e.g., a table), whereby one dimension of the data structure (e.g., rows) corresponds to individual samples 112, and the second dimension (e.g., columns) of the data structure corresponds to nucleobase locations with respect to the reference sequence. In this way, a segment of a genetic sequence can be referenced by a sequence identifier, a starting nucleobase position, and an ending nucleobase position of the segment of the genetic sequence.

The data storage system 200 is further configured to separate the alignment file 260 into groups 270. A group 270 is a subsection of the alignment file 260 that includes segments of genetic sequences from some or all of the samples 112. For example, if the reference sequence includes 20 positions (e.g., 1-20), the data storage system 200 may separate the alignment file 260 into groups 270 having a width of ten nucleobases apiece. In such an example, the data storage system 200 can separate the alignment file 260 into two groups 270, whereby the first group 270 contains the nucleobases at positions 1-10 and the second group 270 contains the nucleobases at positions 11-20. In some scenarios, a sequence of a particular sample 112 may contain gaps between nucleobases, may begin at a later position with respect to the reference sequence, and/or may end before the end of the reference sequence. For example, in a sequence often positions, the third position may be left empty. When determining the groups 270, the data storage system 200 treats the gaps as if the gaps contained a nucleobase. Put another way, when a nucleotide is not present at a particular location of a sample 112, the resultant group 270 can include a gap at the particular location in the row corresponding to the sample 112.

Figure 1B:
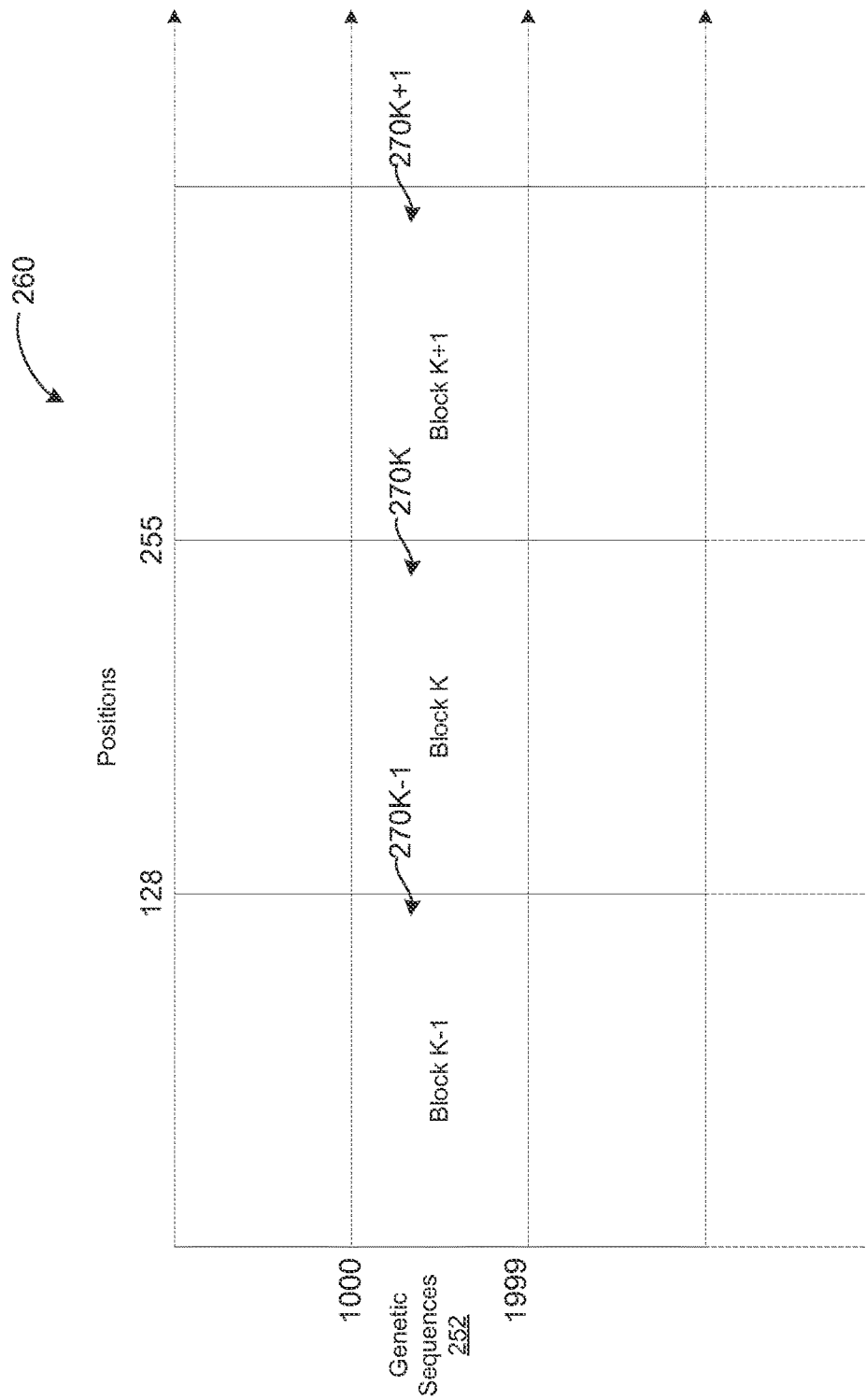
FIG. 1B is a schematic view illustrating an example alignment file.

FIG. 1B illustrates an example of an alignment file 260 separated into at least nine groups 270. In the illustrated example, the alignment file 260 has a width of at least 384 nucleobases and includes at least 3000 sequences (i.e., samples 112). Each group 270 has a length of 128 nucleobases and a height of 1000 gene sequences. In this example, the $K^{th}$ group 270K has the range of positions [128 . . . 255] with respect to a reference sequence and a range of gene sequences [1000 . . . 1999] and the $K+1^{th}$ group 270K+1 has a range of positions [256 . . . 383] with respect to the reference sequence and a range of gene sequences [1000 . . . 1999]. The K−1 group 270K−1 has a range of positions [0 . . . 128]. In this way, the data storage system 200 can identify a group 270 given a sequence identifier and a position with respect to the reference sequence. For instance, in the example of FIG. 1B, if the sequence identifier is 200 and the sequence position is 300, the data storage system 200 determines that the corresponding group is the $K^{th}$ group 270. An alignment file 260 may have any suitable width and/or height, and each group 270 may have any suitable width or height. The dimensions of the groups 270 in FIG. 1B are provided for example only.

In some implementations, the data storage system 200 transposes each group 270 into a transposed group 280, such that the rows of the group 270 become columns in the transposed group 280 and the columns of the group 270 become rows in the transposed group 280. In some of these implementations, the data storage system 200 generates a group string 282 for each transposed group 280. In some implementations, the data storage system 200 can append the contents of each row of a transposed group 280 to a string in a predetermined order. For instance, the data storage system 200 can begin by adding the contents of the first row of the transposed group 280 to an empty group string 282 and can append the contents of each subsequent row of the transposed group 280 to the end of group string 282. In this way, each transposed group 270 can be represented by a group string 282. In some implementations, the group string 282 is delimited using row delimiters, whereby each row delimiter indicates where a new row starts.

In some implementations, the data storage system 200 can create a master string 284 representing the alignment file 260 based on the group strings 282 corresponding to the collection of transposed groups 280. In some examples, the data storage system 200 amends the group strings 282 representing the transposed groups 280 to one another to create a master string 284. For instance, the data storage system 200 can append a first group string 282 to an empty master string 284 and can amend subsequent group strings 282 to the master string 284 in a predetermined order. In some implementations, the master group string 282 is delimited using group delimiters, whereby each group delimiter indicates where a new group string 282 of a transposed group 270 begins. Each group delimiter can further identify the group 270 (or transposed group 280) to which the group string 282 corresponds.

In some implementations, the data storage system 200 can compress the individual groups 270 of the alignment file 260, the transposed groups 280, group strings 282 representing transposed groups 270, or the master string 284 into a compressed file 290. The data storage system 200 can compress any of the above using any suitable compression algorithm. In some implementations, the data storage system 200 compresses the alignment file 260, the transposed groups 270, group strings 282 representing transposed groups 280, or the master string 284 using the Flate or Deflate compression algorithms. The transposition of the groups 270 and subsequent string representation creates a large amount of locality, which is conducive to greater compression rates. Locality is a similarity among DNA sequences represented by alignments of several genetic sequences. A locality value can be expressed or measured as an amount of similarity.

The data storage system 200 is further configured to service read requests 140 for genetic sequence data 114. The data storage system 200 can receive read requests 140 for a segment of a genetic sequence 252. In some implementations, the data storage system 200 identifies one or more compressed files 290 that contain the requested genetic sequence data 114. The data storage system 200 can decompress each of the identified compressed files 290. The data storage system 200 can then reassemble the groups 270 based on the results of decompression. For instance, the data storage system 200 can decompress a compressed file 290 into a master string 284 and identify one or more group strings 282 in the master string 284 that contain the requested genetic sequence data 114. For each of the one or more group strings 282, the data storage system 200 can reassemble a corresponding transposed group 280 based on the identified group string 282. The data storage system 200 can then de-transpose the transposed groups 280 to obtain one or more relevant groups 270. The data storage system 200 can read the requested genetic sequence data 114 from the one or more groups 270. The data storage system 200 can obtain the requested genetic sequence data 114 from one or more groups 270 or from the reassembled alignment file 260. The data storage system 200 can transmit the requested genetic sequence data 114 to the requesting computing device 100.

Figure 2A:
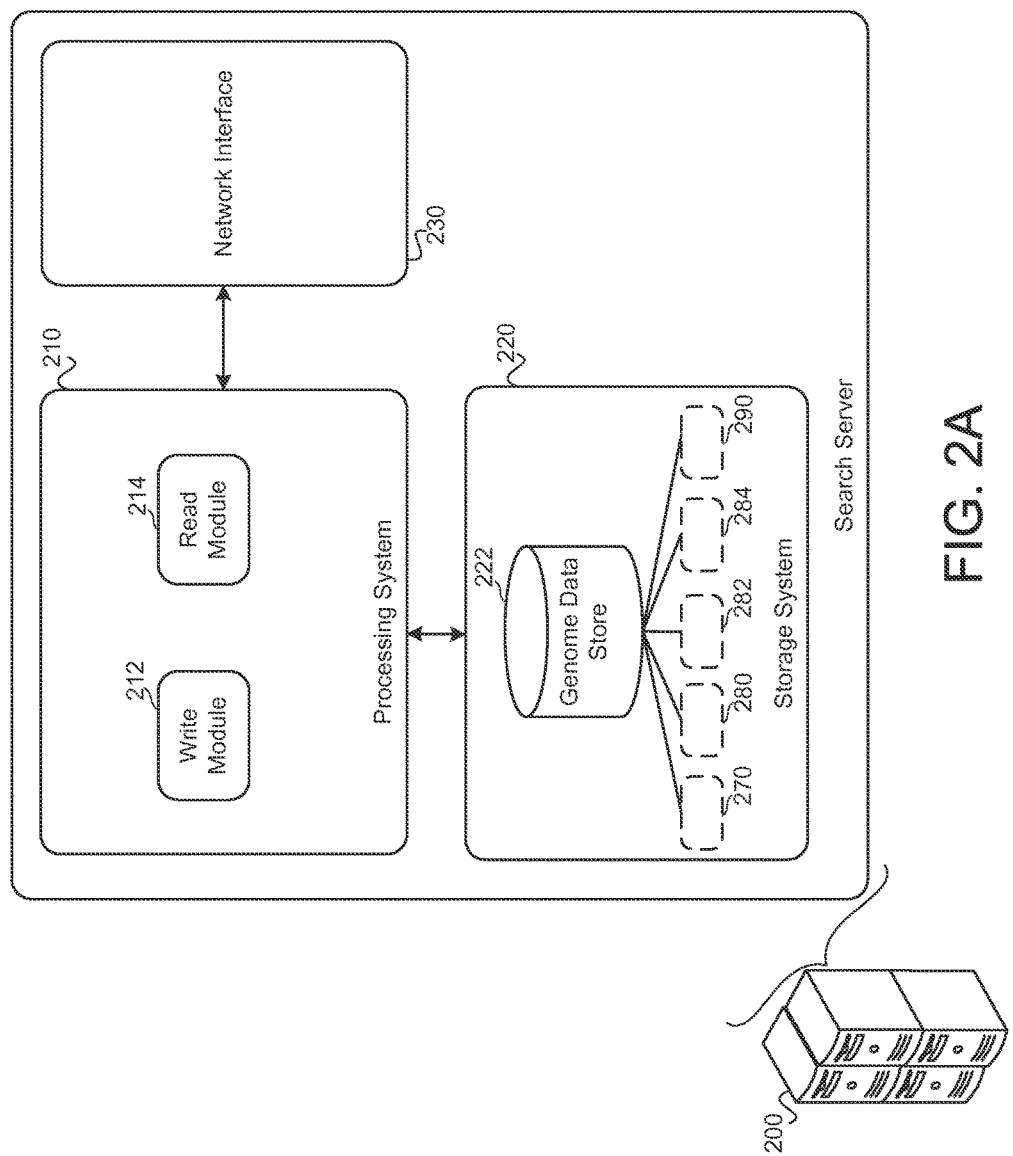
FIG. 2A is a schematic view illustrating an example data storage system.
Figure 2B:
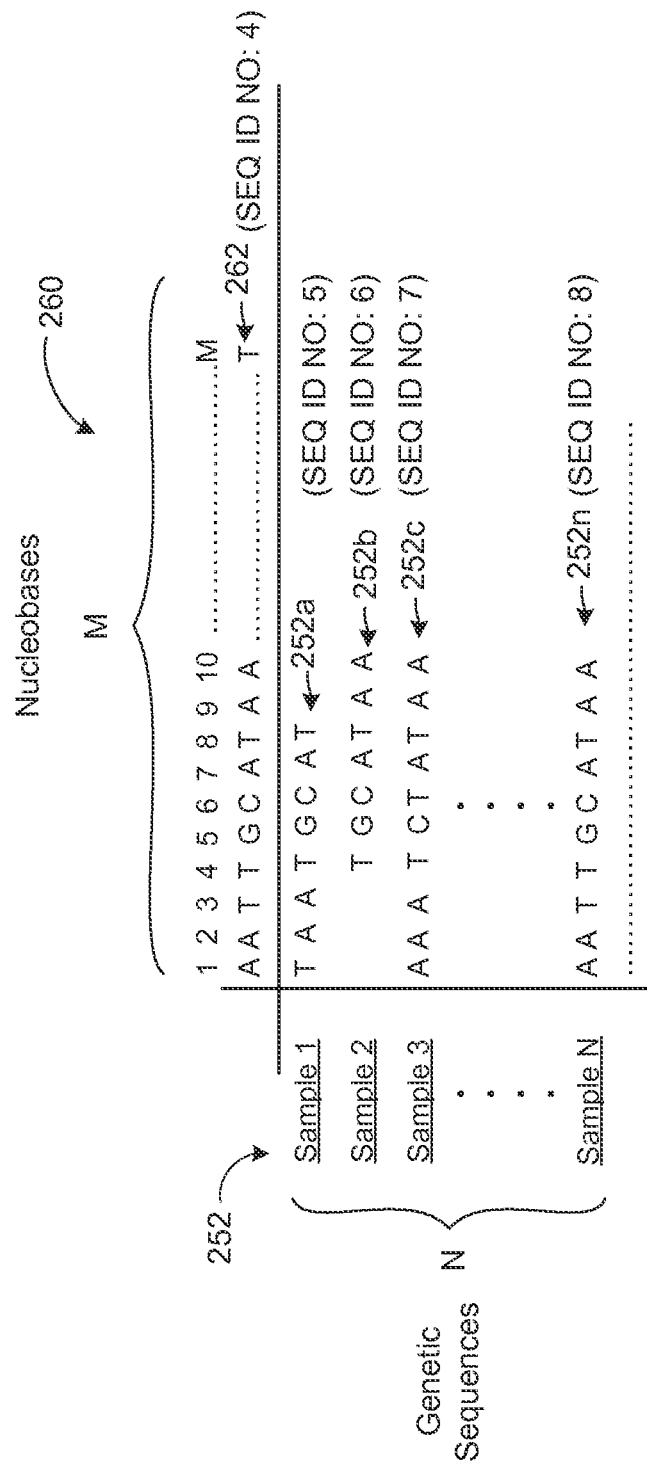
FIG. 2B is a schematic view illustrating an example alignment file.

FIG. 2A illustrates an example data storage system 200. In some implementations, the data storage system 200 is a distributed storage system that includes one or more servers. In other implementations, the data storage system 200 is a standalone server. The data storage system 200 includes a processing system 210, a storage system 220, and a network interface 230.

The processing system 210 can include one or more processing devices, each of which include one or more processors and one or more memory devices (e.g., RAM and/or ROM). In implementations where the processing system 210 includes more than one processing device, the processing devices can operate in a distributed or individual manner. The processing system 210 can execute a write module 212 and a read module 214.

The storage system 220 includes one or more non-transitory computer readable mediums. Examples of non-transitory computer readable mediums include, but are not limited to hard disk drives and solid state drives such as flash memory drives. The storage system 200 can include a genome data store 222. The genome data store 222 may include one or more databases, indices, files, or other data structures that store genetic sequence data 114. The genome data store 220 can store alignment files 260, groups 270, transposed groups 280, group strings 282 representing transposed groups 280, master strings 284, and/or compressed files 290.

The network interface 230 includes one or more devices that are configured to communicate with the network 120. The network interface 230 can include one or more transceivers for performing wired or wireless communication. Examples of the network interface 230 can include, but are not limited to, a transceiver configured to perform cellular communications (e.g., transmission using the third generation (3G) or fourth generation (4G) telecommunications standards), a transceiver configured to perform communications using the IEEE 802.11 wireless standard, a Bluetooth transceiver, an Ethernet port, a wireless transmitter, and a universal serial bus (USB) port.

The write module 212 receives genome files 250 from one or more source computing devices 100 and stores the genetic sequence data 114 contained in the genome files 250 in the genome data store 222. The write module 212 receives N genome files 250 (e.g., BAM files or SAM files), where N is an integer greater than or equal to two. The write module 212 creates an alignment file 260 based on the genetic sequence data 114 contained in the N genome files 250. FIG. 2B illustrates an example of an alignment file 260. In the example of FIG. 2B, the alignment file 260 includes N rows and M columns. N is equal to the number of individual gene sequences 252, 252a-n represented in the alignment sequence. M is equal to the maximum number of nucleobases in the reference sequence 262. Each gene sequence 252 can have a length that is less than or equal to M nucleobases. For example, the second gene sequence 252b, begins at position 4 and ends at position 10. Therefore, the second gene sequence 252b has a length of seven nucleobases.

The write module 212 separates the alignment file 260 into a set of groups 270. Each group 270 is a block of the alignment file 260 having X columns and Y rows. The values of X and Y can be assigned by a developer or can be determined heuristically. FIG. 2C illustrates an example of an alignment file 260 that has been separated into two groups 270a, 270b. In FIG. 2C, the write module 212 separates the alignment file 260 into a first group 270a and a second group 270b. Each group 270a, 270b has a length of five nucleobases and a height of three gene sequences 252.

In some implementations, the write module 212 transposes each group 270 of an alignment file 260. FIG. 2D illustrates an example of transposed groups 270. In FIG. 2D, the write module 212 transposes each group 270a, 270b into transposed groups 280, 280a, 280b, such that the columns in each transposed group 280a, 280b represent segments of gene sequences 252, and the rows of each transposed group 280a, 280b represent nucleobase positions. As shown in FIGS. 2C and 2D, gaps existing in a group 270 are preserved in the transposed groups 280.

The write module 212 may be further configured to create a group string 282 for each transposed group 280. In these implementations, the write module 212 appends the contents of each subsequent row to the end of the group string 282. Initially, the write module 212 appends the contents of the first row of a transposed group 280 to an empty group string 282. The write module 212 can then iteratively append the contents of each subsequent row to the group string 282. Furthermore, when a row contains one or more empty positions or gaps, the write module 212 inserts a space in the group string 282. Drawing from the example of FIG. 2D, a string corresponding to the first transposed group 280a is "T_AA_AA_ATTTGGC" (SEQ ID NO: 1) and a group string 282 corresponding to the second transposed group 280b is "CCTAAATT_AA_AA" (SEQ ID NO: 2). In some implementations, the write module 212 can insert row delimiters in the group strings 282 to indicate the beginning of a new row.

The write module 212 may be further configured to generate a master string 284 based on the generated group strings 282. In some implementations, the write module 212 appends each group string 282 to the master string 284. Initially, the write module 212 appends the first group string 282 to an empty master string 284. The write module 212 can then iteratively append each subsequent group string 282 to the master string 284. Continuing from the example of FIG. 2D, a master string 284 resulting from appending the group string 282 of the second transposed group 280b to the group string 282 of the first transposed group 270a can be represented by: "T_AA_AA_ATTTGGCCCTAAATT-T_AA_AA" (SEQ ID NO: 3).

In some implementations, the write module 212 can insert group delimiters in the master string 284 to indicate the beginning of a new transposed group 280.

While the example of FIGS. 2B-2D illustrate gene sequences 252 of relatively short length (i.e., 10 nucleobases), the write module 212 can be configured to operate on gene sequences 252 having any suitable length and alignment files 260 having any suitable number of gene sequences 252. In some implementations, the length of a reference sequence 262 should be selected based on a desired number of groups 270, such that the length of the reference sequence 262 is divisible by the desired number of groups 270.

In some implementations, the writing module 212 compresses the individual group strings 282 or the master string 284 to obtain one or more compressed files 290. The writing module 212 can utilize any suitable compression algorithm, including Flate or Deflate. In some implementations, the writing module 212 compresses the group strings 282 or master string 284 using the Flate algorithm with the compression level set to nine. The writing module 212 can write the compressed files 290 to the genome data store 222.

In some implementations, the writing module 212 compresses the groups 270 or transposed groups 280 to obtain a compressed file 290. In these implementations, the writing module 212 does not generate group strings 282 or a master string 284. The writing module 212 can compress the groups 270 or transposed groups 280 using the Flate or Deflate compression algorithms. The writing module 212 can store the compressed file 290 in the genome data store 222.

In some implementations, the writing module 212 can encrypt the compressed file 290 prior to storing the compressed file 290. The writing module 212 can utilize any suitable encryption algorithm to encrypt the compressed file 290.

The read module 214 receives read requests 140 to read specific genetic sequence data 114. In some implementations, a read request 140 can include a sequence identifier and a read offset. The sequence identifier can indicate a particular gene sequence 252 to which the requested segment belongs. The read offset can indicate a particular location with respect to the reference sequence 262, a group 270 where the requested segment of the requested gene sequence 252 is stored, or a position with respect to the reference sequence 262 at which a requested segment begins. In the latter implementations, the read request 140 can further include an ending location that indicates the location of the last nucleobase to be read. In this way, a read request 140 may implicate more than one group 270, if the requested segment of gene sequence 252 spans more than one group 270.

The read module 214 can obtain one or more compressed files 290 that contain the requested gene sequence data 114 and can identify the individual group strings 282 that represent the alignment file 260. In implementations where the write module 212 encrypts the compressed files 290, the read module 214 decrypts the compressed files 290 prior to identifying the individual group strings 282.

In implementations where the compressed file 290 contains a master string 284, the read module 214 retrieves a compressed file 290 containing the master string 284 corresponding to the requested gene sequence data 114. The read module 214 decompresses the compressed file 290 to obtain the master string 284. The read module 214 then identifies the individual group strings 282 that make up the master string 284. In some implementations, the read module 214 uses the group delimiters embedded in the master string 284 to identify the individual group strings 282 contained in the master string 284. The read module 214 can then identify relevant group strings 284 based on the sequence identifier, the read offset, and in some implementations, the ending location. The read module 214 can utilize the values contained in the read request 140 to identify one or more particular group strings 282 that contain the requested genetic sequence data 114. For instance, a first group string 282 may correspond to positions [0 . . . 9] with respect to a reference sequence 262 and may contain segments of genetic sequences [1 . . . 4] and a second group string 282 may correspond to positions [10 . . . 19] and may contain segments of sequences [1 . . . 4]. If a read request 140 contains a sequence identifier two (2) and a read offset four (4), the read module 212 can identify the first group string 282 as being the relevant group string 282. Similarly, if the read request 140 contains a sequence identifier two (2), a read offset four (4), and an ending location of six (6), the read module 212 can identify the first group string 282 and the second group string 282 as being the relevant group strings 282.

When compressed files 290 respectively contain individual group strings 282, the read module 214 obtains one or more compressed files 290 that contain the requested genetic sequence data 114. In particular, the read module 214 can determine one or more relevant group string 282 (i.e., contain the requested genetic sequence data 114) based on the sequence identifier, the read offset, and in some implementations, the ending location, in the manner described above. The read module 212 can then retrieve one or more compressed files 290 respectively containing the one or more relevant group strings 282. The read module 212 can decompress the one or more compressed files 290 to obtain the one or more relevant group strings 282.

For each of the one or more relevant group string 282, the read module 214 can reconstruct a transposed group 280 based on the contents of the group string 282. In some implementations, the read module 214 utilizes the row delimiters in the group string 282 to identify each row of the transposed group 280. Based on the identified rows in a group string, the read module 214 reconstructs a transposed group 280.

In some implementations, the read module 214 can detranspose each of the one or more transposed groups 280 to obtain one or more relevant groups 270 of the alignment file 260. The read module 214 can read the requested segment of the gene sequence 252 from the relevant group or groups 270 using the sequence identifier. In some implementations, the read module 214 reads the entire genetic sequence 252 contained in a relevant group 270 (i.e., the genetic sequence 252 indicated by the sequence identifier). In other implementations, the read module 214 begins reading a genetic sequence 252 at a location indicated by the read offset and continues reading until the ending location. The read module 214 can transmit the read genetic sequence data 114 to the requesting computing device 130. In some implementations, the read module 214 generates a genomic file 250 (e.g., a BAM file) containing the read genetic sequence data 114 and transmits the generated genomic file 250 to the requesting computing device 130.

The techniques described with respect to FIGS. 2A-2D are provided for example. Variations of the techniques are contemplated and are within the scope of the disclosure.

Figure 3:
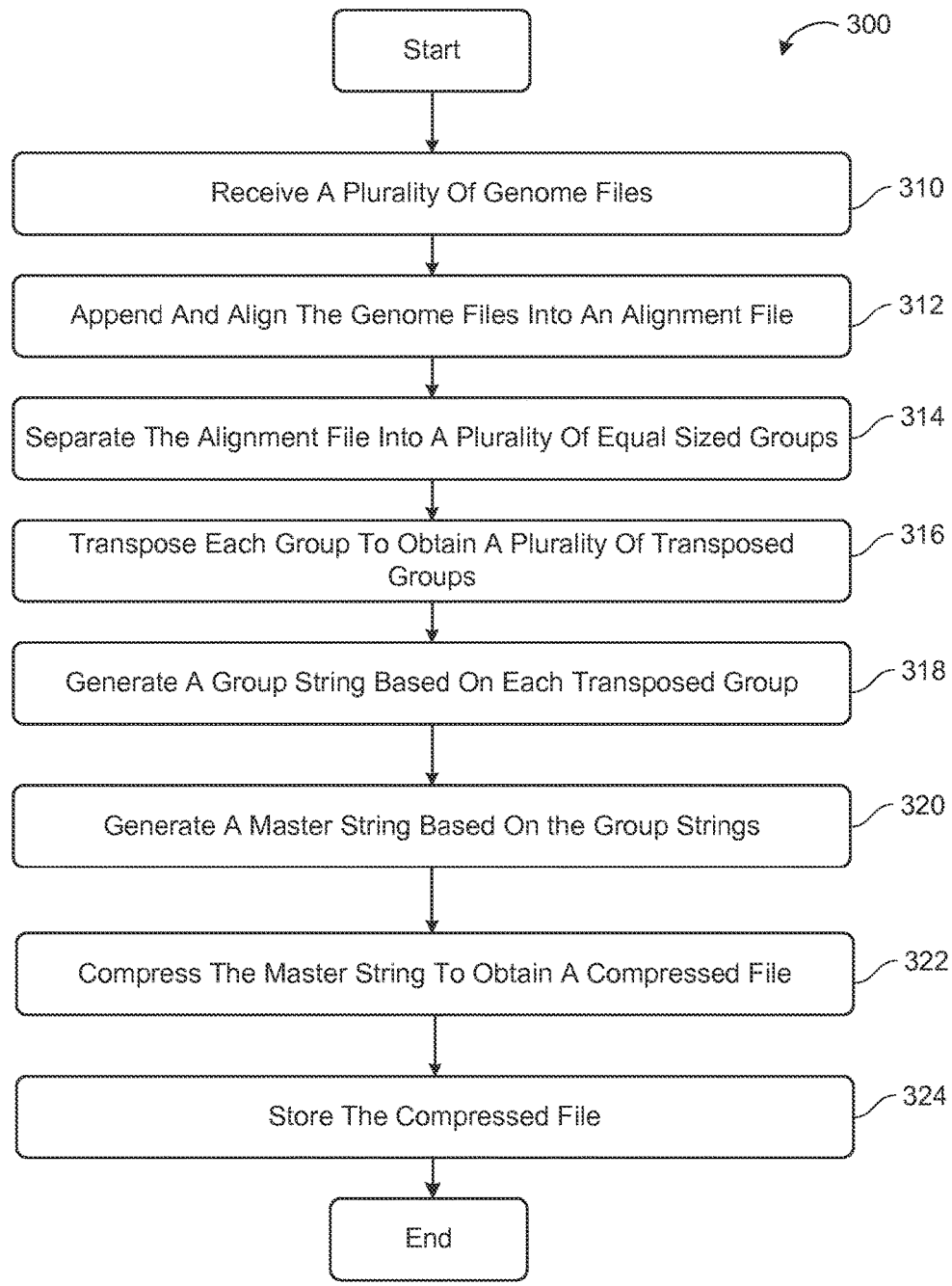
FIG. 3 is a flow chart illustrating an example set of operations for a method for storing gene sequence data in the data storage system.

Referring now to FIG. 3, an example set of operations for a method 300 for writing a set of gene sequences 252 is disclosed. For purposes of explanation, the method 300 is described with respect to the components of the data storage system 200 of FIG. 2A.

At operation 310, the processing system 210 receives a plurality of genome files 250 from one or more source computing devices 100. Each genome file 250 can represent a gene sequence 252 corresponding to a sample 112. In some scenarios, the genome files 250 are BAM files, where the genetic sequence data 114 contained therein is aligned to a reference sequence 262.

At operation 312, the processing system 210 generates an alignment file 260 based on the received genome files 250. The processing system 210 can identify the gene sequence 252 from each genome file 250 and can align each gene sequence 252 to a reference sequence 262 of the alignment file 260. In some implementations, the processing system 210 may determine a "best fit" alignment for each gene sequence 252.

At operation 314, the processing system 210 separates the alignment file 260 into a plurality of equal sized groups 270. Each group 270 can have X columns and Y rows, where X and Y can be any suitable positive integers. At operation 316, the processing system 210 transposes each group 270 into a transposed group 280.

At operation 318, the processing system 210 generates a group string 282 for each transposed group 280. For each transposed group 280, the processing system 210 can begin a group string 282 with the first row of the transposed group 270 and can iteratively append the contents of each subsequent row to the group string 282. In some implementations, the processing system 210 embeds a row delimiter to the group string 282 each time a new row is appended to the group string 282.

At operation 320, the processing system 210 generates a master string 284 based on the group strings 282. The processing system 210 can begin with a group string 282 corresponding to a first transposed group 280 and can iteratively append subsequent group strings 282 corresponding to subsequent transposed groups 280 to the master string 284. In some implementations, the processing system 210 embeds a group delimiter to the master string 284 each time a new group string 282 is appended to the master string 284.

At operation 322, the processing system 210 compresses the master string 284. The processing system 210 can utilize any suitable compression algorithm. In some implementations, the processing system 210 utilizes Flate to compress the master string 284 into a compressed file 290. At operation 324, the processing system 210 stores the compressed file 290 in the genome data store 222. In some implementations, the processing system 210 encrypts the compressed file 290 prior to storing the compressed file 290.

Some of the operations described are optional and variations of the method 300 are contemplated. For instance, the processing system 210 may be configured to compress individual group strings 282, transposed groups 280, or groups 270 into compressed files 290.

Figure 4:
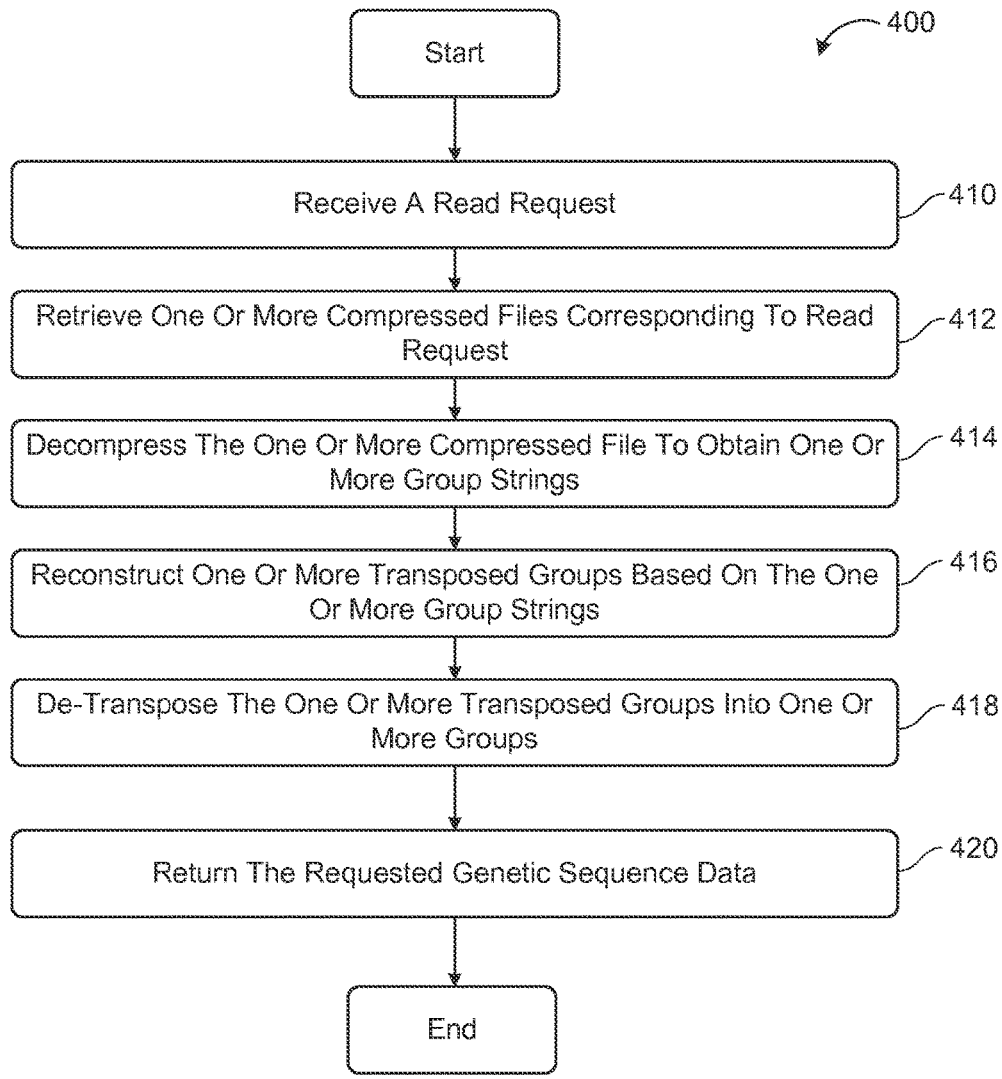
FIG. 4 is a flow chart illustrating an example set of operations for a method for reading gene sequence data from the data storage system.

FIG. 4 illustrates an example set of operations for a method 400 for performing a read operation. For purposes of explanation, the method 400 is described with respect to the components of the data storage system 200 of FIG. 2A.

At operation 410, the processing system 210 receives a read request 140 from a requesting computing device 130. The read request 140 can include a sequence identifier and a read offset. The sequence identifier indicates a particular gene sequence 252. In some implementations, the read offset can indicate a particular location with respect to the reference sequence 262 or can indicate a particular group 270. In other implementations, the read offset can indicate a starting position in the reference sequence 262 where the requested segment of the particular genetic sequence 252 begins. In these implementations, the read request 140 can further include an ending location for the requested segment.

At operation 412, the processing system 210 retrieves one or more compressed file 290 that contain the requested gene sequence 252 from the genome data store 222. In some implementations, the processing system 210 decrypts the compressed file 290 after retrieving the compressed file 290. At operation 414, the processing system 210 decompresses the one or more compressed files 290. The processing system 210 can decompress the compressed files 290 using the Deflate algorithm. In some implementations, the processing system 210 decompresses a compressed file 290 to obtain a master string 284. In these implementations, the processing system 210 can parse the master string 284 to identify one or more group strings 282, each group string 282 corresponding to a different transposed group 280.

In some implementations, each of the compressed files 290 respectively corresponds to a different transposed group 280 and contains an individual group string 282. In these implementations, the processing system 210 determines one or more group strings 280 that are relevant based on the sequence identifier, the read offset, and in some implementations, the ending location. The processing system 210 retrieves one or more compressed files 290 containing the relevant group strings 282 and decompresses each of the one or more transposed groups 280 to obtain the one or more relevant group strings 282.

At operation 416, the processing system 210 reconstructs one or more transposed groups 280 based on the one or more relevant group strings 282. For each relevant group string 282, the processing system 210 can reconstruct the transposed group 280 corresponding thereto. A group string 282 is relevant if it contains at least one nucleobase of the requested genetic sequence data. Put another way, the processing system 210 only needs to reconstruct a transposed group 280 if the transposed group 280 contains the requested data. At operation 418, the processing system 210 can de-transpose each transposed group 280 into a respective group 270.

At operation 420, the processing system 210 returns the requested genome data. In implementations where the read offset indicates a position or a group 270, the processing system 210 reads the entire segment of the genetic sequence 252 that spans across the group 270 indicated by the read offset. For example, if the read offset references a position within a certain group 270, the processing system 210 reads the entire genetic sequence 252 (indicated by the sequence identifier) contained within the group 270. In implementations where the read request 140 includes a read offset and an ending location, the processing system 210 reads the segment of the genetic sequence 252 indicated by the read request 140 that begins at the position indicated by the read offset and ends at the ending location. In some scenarios, the processing system 210 reads the segment across multiple groups 270. The processing system 210 can generate a genome file 250 based on the read segment of the genetic sequence 252. The processing system 210 can return the genome file 250 to the requesting computing device 130 via the network interface 230.

The methods 300, 400 are provided for example only and not intended to limit the scope of the disclosure. Variations of the methods 300, 400 are contemplated.

Various implementations of the systems and techniques described here can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method comprising:

receiving, by a processing device, a plurality of genome files, each genome file corresponding to a different sample and defining a genetic sequence;

selecting, by the processing device, a number of nucleobases for a reference sequence;

generating, by the processing device, a two-dimensional alignment file based on the genome files and the reference sequence, wherein a first dimension of the alignment file corresponds to individual genetic sequences and each of the genetic sequences having nucleobases aligned with respect to corresponding nucleobases of the reference sequence along a second dimension of the alignment file;

separating, by the processing device, the alignment file into a target number of groups, each group being a subsection of the alignment file and containing segments of the genetic sequences of two or more of the genomic files;

for each group, transposing, by the processing device, the group into a transposed group such that the segments of each genetic sequence in the transposed group are aligned with a corresponding portion of the reference sequence along the first dimension resulting in a corresponding locality defined as a measure of similarity of genetic sequences;

for each transposed group, generating, by the processing device, a group string based on the transposed group, the group string comprising contents of the transposed group;

generating, by the processing device, a master string based on the group strings, the master string representing the entire contents of the alignment file;

compressing, by the processing device, the master string into a compressed file; and storing, by the processing device, the compressed file in a non-transitory genome data store, wherein the corresponding localities of the transposed groups satisfy a threshold locality conducive for a threshold file compression of the master string.

2. The method of claim 1, wherein storing the groups further comprises storing the transposed groups in the genome data store.

3. The method of claim 2, wherein storing the transposed groups further comprises:

compressing the group strings into group-string compressed files; and storing the group-string compressed files in the genome data store.

4. The method of claim 3, wherein the group strings are compressed using a Flate compression algorithm.

5. The method of claim 3, wherein the master string is compressed using a Flate algorithm.

6. The method of claim 1, wherein the plurality of genome files comprise binary sequence alignment/map (BAM) files.

7. The method of claim 1, wherein the number of nucleobases for the reference sequence is selected to be divisible by the target number of groups of the alignment file.

8. The method of claim 1, further comprising:

receiving, at the processing device, a read request for a portion of the genetic sequence; and in response to receiving the read request:

decompressing, by the processing device, the master string; and transmitting, by the processing device, the portion of the genetic sequence.

9. The method of claim 1, further comprising compressing, by the processing device, each group string into group-string compressed files.

10. The method of claim 9, further comprising:

receiving, at the processing device, a read request for a portion of the genetic sequence; and in response to receiving the read request:
- identifying, by the processing device, a subset of group-string compressed files that each include at least a portion of the requested portion of the genetic sequence;
- decompressing, by the processing device, the identified subset of group-string compressed files into decompressed group strings; and
- transmitting, by the processing device, the portion of the genetic sequence.

11. The method of claim 10, wherein identifying the subset of group-string compressed files comprises decompressing the master string.

12. The method of claim 10, further comprising reassembling, by the processing device, the decompressed group strings based on results of the decompression.

13. The method of claim 12, wherein reassembling the decompressed group strings further comprises, for each group string of the decompressed group strings, reassembling a corresponding transposed group based on the respective group string.

14. The method of claim 13, wherein reassembling the decompressed group strings further comprises de-transposing the transposed groups to obtain one or more de-transposed groups.

* * * * *

SEQUENCE LISTING

```
<160> NUMBER OF SEQ ID NOS: 8

<210> SEQ ID NO 1
<211> LENGTH: 12
<212> TYPE: DNA
<213> ORGANISM: Artificial Sequence
<220> FEATURE:
<223> OTHER INFORMATION: Synthetically generated nucleotide

<400> SEQUENCE: 1
taaaaatttg gc                                                        12

<210> SEQ ID NO 2
<211> LENGTH: 13
<212> TYPE: DNA
<213> ORGANISM: Artificial Sequence
<220> FEATURE:
<223> OTHER INFORMATION: Synthetically generated nucleotide

<400> SEQUENCE: 2
cctaaattta aaa                                                       13

<210> SEQ ID NO 3
<211> LENGTH: 25
<212> TYPE: DNA
<213> ORGANISM: Artificial Sequence
<220> FEATURE:
<223> OTHER INFORMATION: Synthetically generated nucleotide

<400> SEQUENCE: 3
taaaaatttg gccctaaatt taaaa                                          25

<210> SEQ ID NO 4
<211> LENGTH: 10
<212> TYPE: DNA
<213> ORGANISM: Artificial Sequence
<220> FEATURE:
<223> OTHER INFORMATION: Synthetically generated nucleotide

<400> SEQUENCE: 4
aattgcataa                                                           10

<210> SEQ ID NO 5
<211> LENGTH: 8
<212> TYPE: DNA
<213> ORGANISM: Artificial Sequence
<220> FEATURE:
<223> OTHER INFORMATION: Synthetically generated nucleotide

<400> SEQUENCE: 5 taatgcat                                                              8

<210> SEQ ID NO 6
<211> LENGTH: 7
<212> TYPE: DNA
```

```
<213> ORGANISM: Artificial Sequence
<220> FEATURE:
<223> OTHER INFORMATION: Synthetically generated nucleotide

<400> SEQUENCE: 6 tgcataa                                                                 7

<210> SEQ ID NO 7
<211> LENGTH: 10
<212> TYPE: DNA
<213> ORGANISM: Artificial Sequence
<220> FEATURE:
<223> OTHER INFORMATION: Synthetically generated nucleotide

<400> SEQUENCE: 7
aaatctataa                                                             10

<210> SEQ ID NO 8
<211> LENGTH: 10
<212> TYPE: DNA
<213> ORGANISM: Artificial Sequence
<220> FEATURE:
<223> OTHER INFORMATION: Synthetically generated nucleotide

<400> SEQUENCE: 8
aattgcataa                                                             10
```